United States Patent [19]
Benson

[11] Patent Number: 5,919,165
[45] Date of Patent: Jul. 6, 1999

[54] ROTATABLE NEEDLE SHIELD FOR NEEDLE CANNULA

[75] Inventor: Carl L. Benson, Wyckoff, N.J.

[73] Assignee: Becton, Dickinson and Company, Franklin Lakes, N.J.

[21] Appl. No.: 08/938,096

[22] Filed: Sep. 26, 1997

[51] Int. Cl.$^6$ .................................................. A61M 5/00
[52] U.S. Cl. .......................... 604/110; 604/192; 604/263
[58] Field of Search ................................... 604/110, 187, 604/192, 198, 263; 128/919

[56] References Cited

U.S. PATENT DOCUMENTS

| | | | |
|---|---|---|---|
| 3,658,061 | 4/1972 | Hall | 128/214.4 |
| 4,664,259 | 5/1987 | Landis | 206/365 |
| 4,867,746 | 9/1989 | Dufresne | 604/192 |
| 4,872,552 | 10/1989 | Unger | 206/365 |
| 4,883,469 | 11/1989 | Glazier | 604/192 |
| 4,886,503 | 12/1989 | Miller | 604/192 |
| 4,909,791 | 3/1990 | Norelli | 604/192 |
| 4,909,792 | 3/1990 | Norelli | 604/192 |
| 4,944,397 | 7/1990 | Miller | 206/365 |
| 4,944,731 | 7/1990 | Cole | 604/192 |
| 4,950,249 | 8/1990 | Jagger et al. | 604/192 |
| 4,976,699 | 12/1990 | Gold | 604/192 |
| 4,982,842 | 1/1991 | Hollister | 206/365 |
| 5,011,475 | 4/1991 | Olson | 604/192 |
| 5,116,325 | 5/1992 | Paterson | 604/192 |
| 5,135,509 | 8/1992 | Olliffe | 604/192 |
| 5,139,489 | 8/1992 | Hollister | 604/192 |
| 5,151,089 | 9/1992 | Kirk, III et al. | 604/192 |
| 5,188,611 | 2/1993 | Orgain | 604/192 |
| 5,207,653 | 5/1993 | Janjua et al. | 604/192 |
| 5,232,454 | 8/1993 | Hollister | 604/192 |
| 5,232,455 | 8/1993 | Hollister | 604/192 |
| 5,242,417 | 9/1993 | Paudler | 604/192 |
| 5,312,369 | 5/1994 | Arcusin et al. | 604/192 |
| 5,405,332 | 4/1995 | Opalek | 604/192 |
| 5,486,163 | 1/1996 | Haynes | 604/192 |
| 5,490,841 | 2/1996 | Landis | 604/110 |
| 5,509,907 | 4/1996 | Bevilacqua | 604/263 |

*Primary Examiner*—John D. Yasko
*Attorney, Agent, or Firm*—John L. Voellmicke

[57] ABSTRACT

A needle shield assembly is provided for a needle cannula. The assembly includes a support sleeve, a stop collar and a needle shield. The support sleeve is rotatably mounted in a proximal position about the needle cannula. The stop collar is secured on the needle cannula distally from the support sleeve so that the stop collar traps the support sleeve in a proximal position on the needle cannula. The needle shield is hingedly mounted to the support sleeve for rotation between a first position where the needle shield protectively encloses the needle cannula and a second position where the support sleeve is angularly aligned to and spaced from the needle cannula. The hingedly connected needle shield and support sleeve can be rotated around the needle cannula.

11 Claims, 7 Drawing Sheets

ROTATABLE NEEDLE SHIELD FOR NEEDLE CANNULA

BACKGROUND OF THE INVENTION

1. Field of the Invention

The subject invention relates to hinged needle shields that can be rotated into shielding relationship with a needle cannula for preventing accidental sticks.

2. Description of the Prior Art

A needle cannula is an elongate metal tube having a proximal end, a distal end and a lumen extending between the ends. The proximal end of the needle cannula may be securely engaged in the distal end of a medical implement, such as a hypodermic syringe. Alternatively, the proximal end of the prior art needle cannula may be securely engaged in a needle hub, which in turn is removably engageable with a medical implement. The distal end of the prior art needle cannula typically is beveled to define a sharp point.

Needle cannulas often are used with needle shields to prevent accidental contact with the pointed distal end of the needle cannula. One type of prior art needle shield includes a rigid U-shaped channel having a proximal end, a distal end and a length slightly greater than the length of the needle cannula. The proximal end of the U-shaped channel is hingedly mounted to the needle hub or to some other structure near the proximal end of the needle cannula. Thus the prior art hinged needle shield can be rotated between a first position where the needle cannula is safely enclosed within the hinged needle shield and a second position where the needle cannula is exposed for use.

Hinged needle shields have several very desirable attributes. For example, the prior art hinged needle shield does not require a specially manufactured hypodermic syringe. Thus, the hub of a needle assembly having a hinged needle shield thereon can be connected to a hypodermic syringe in the conventional manner, without affecting the size and feel of the hypodermic syringe. Additionally, the prior art hinged needle shield enables the needle cannula to be easily accessed or shielded. In particular, both shielding and unshielding are carried out by application of digital forces at locations spaced from the distal tip of the needle cannula and in directions transverse to the longitudinal axis of the needle cannula.

One drawback of the prior art hinged needle shield relates to the potential for visual or physical interference when the needle shield is hingedly moved into its open position to permit use of the needle cannula. In particular, a doctor, nurse or other medical technician may want a specified orientation of the bevel on the distal end of the needle cannula to achieve a precise positioning of the point formed by the bevel. Additionally, a specified rotational orientation of the needle cannula may help to gauge the depth of insertion. The hinged needle shield could be fixed on the needle cannula at a rotational orientation that visually obstructs the medical technician's view of the injection site. At other times, the needle shield could contact the patient and thereby prevent the medical technician from having the needle cannula aligned at a small acute angle to the patient.

Some medical procedures require administration of a specified dose of a drug. In these situations, the medical technician may have to closely inspect the volume measuring indicia on the syringe barrel during the injection. Once again, the hinged needle shield could visually obscure the volume measuring indicia.

SUMMARY OF THE INVENTION

The subject invention is directed to a needle shield assembly for use with a needle cannula. The needle cannula includes a proximal end and a pointed distal end. The proximal end may be securely engaged in the distal end of a medical implement or securely engaged in a needle hub that is preferably releasably engageable with a medical implement.

The needle shield assembly of the subject invention comprises an elongate substantially rigid needle shield having a proximal end and a distal end. Portions of the needle shield between the proximal and distal ends may define a generally U-shaped cross-section dimensioned to receive the needle cannula therein.

The proximal end of the needle shield is hinged to a location near the proximal end of the needle cannula for movement about an axis extending substantially orthogonal to the needle cannula. Thus, distal portions of the needle shield can be rotated between a first position where the needle cannula is protectively disposed within the needle shield and a second position where the needle shield is spaced from and angularly aligned to the needle cannula so that the needle cannula may be used. The hinged connection of the needle shield to the location near the proximal end of the needle cannula is rotatable about the axis of the needle cannula. Thus, the angular alignment of the needle shield relative to the needle cannula can be adjusted to ensure that the needle shield does not visually obscure either the distal end of the needle cannula or the volume measuring indicia printed on the medical implement with which the needle cannula and needle shield are used. Additionally, the ability to rotate the hinged connection of the needle shield about the axis of the needle cannula enables the medical technician using the needle cannula and associated medical implement to align the needle cannula in the most efficient and desired manner.

The hinged connection of the needle shield relative to the needle cannula may include a support sleeve rotatably mounted around the proximal end of the needle cannula. The support sleeve may include oppositely directed ears defining hinge pins to which the needle shield may be hingedly connected. The support sleeve may be retained near the proximal end of the needle cannula by a collar secured to the needle cannula by an epoxy bead. The collar may be spaced slightly distally of the support sleeve.

The support sleeve may initially be unitary with the collar. However, a thin frangible connection may extend axially between the initially unitary support sleeve and collar. The thin frangible connection may be severed by merely rotating the support sleeve relative to the collar after the collar has been secured to the needle cannula.

In one embodiment of the present invention a needle shield assembly comprises a needle cannula having a proximal end, a distal end and a lumen therethrough. A support sleeve is rotatably disposed around a portion of the needle cannula. Stop means is positioned between the support sleeve and the distal end of the needle cannula for limiting slidable distal movement of the support sleeve along the needle cannula. A needle shield is connected to the support sleeve for hinged rotation between a first position where the needle shield substantially encloses the needle cannula and a second position where the needle shield is spaced from the needle cannula. The needle shield and the support sleeve are rotatable about the needle cannula into a selected position for facilitating use of the needle cannula.

DETAILED DESCRIPTION OF THE PREFERRED EMBODIMENT

Figure 7:
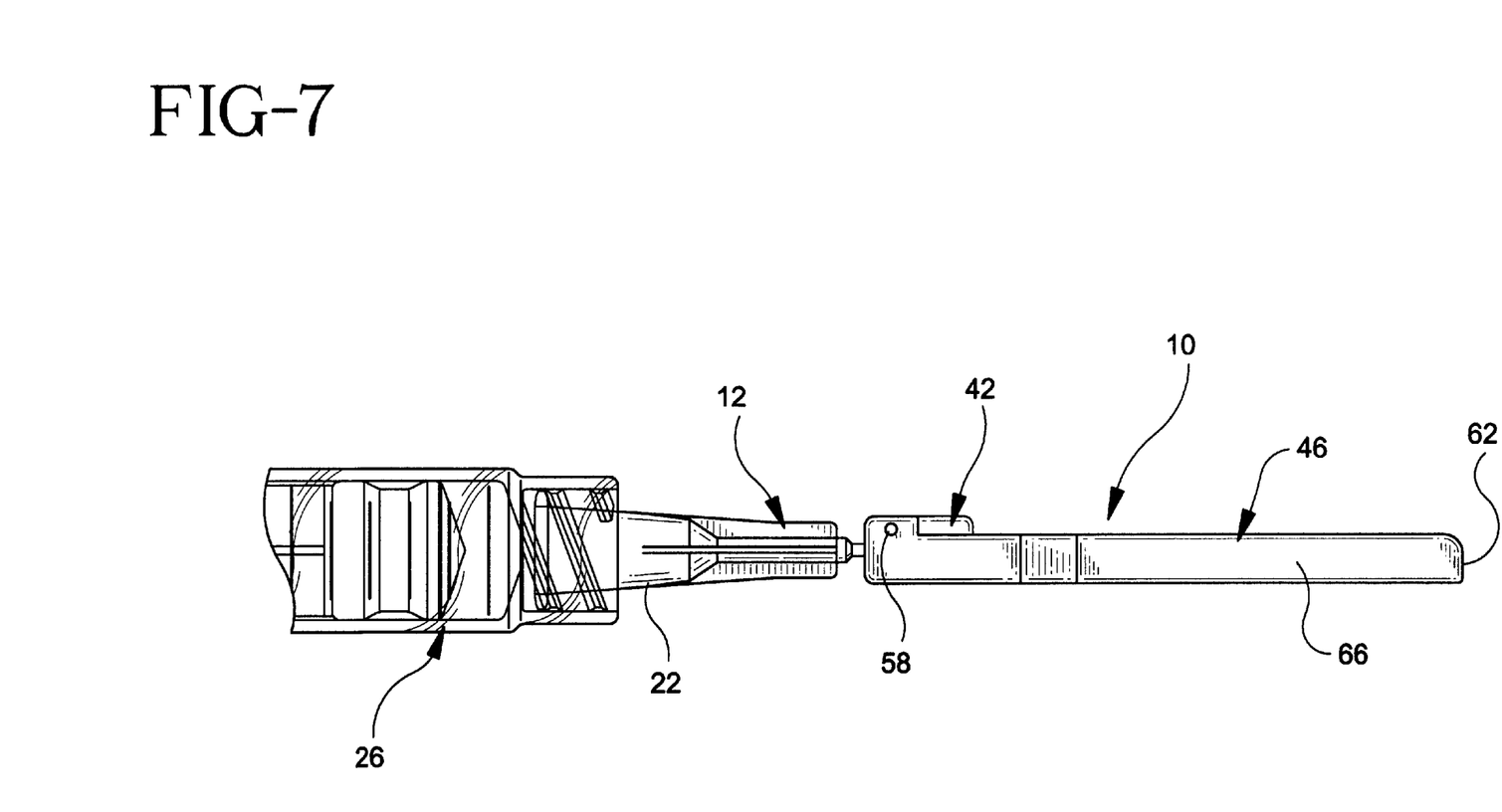
FIG. 7 is a side elevational view similar to FIG. 5, but showing the needle shield mounted to the support sleeve.
Figure 8:
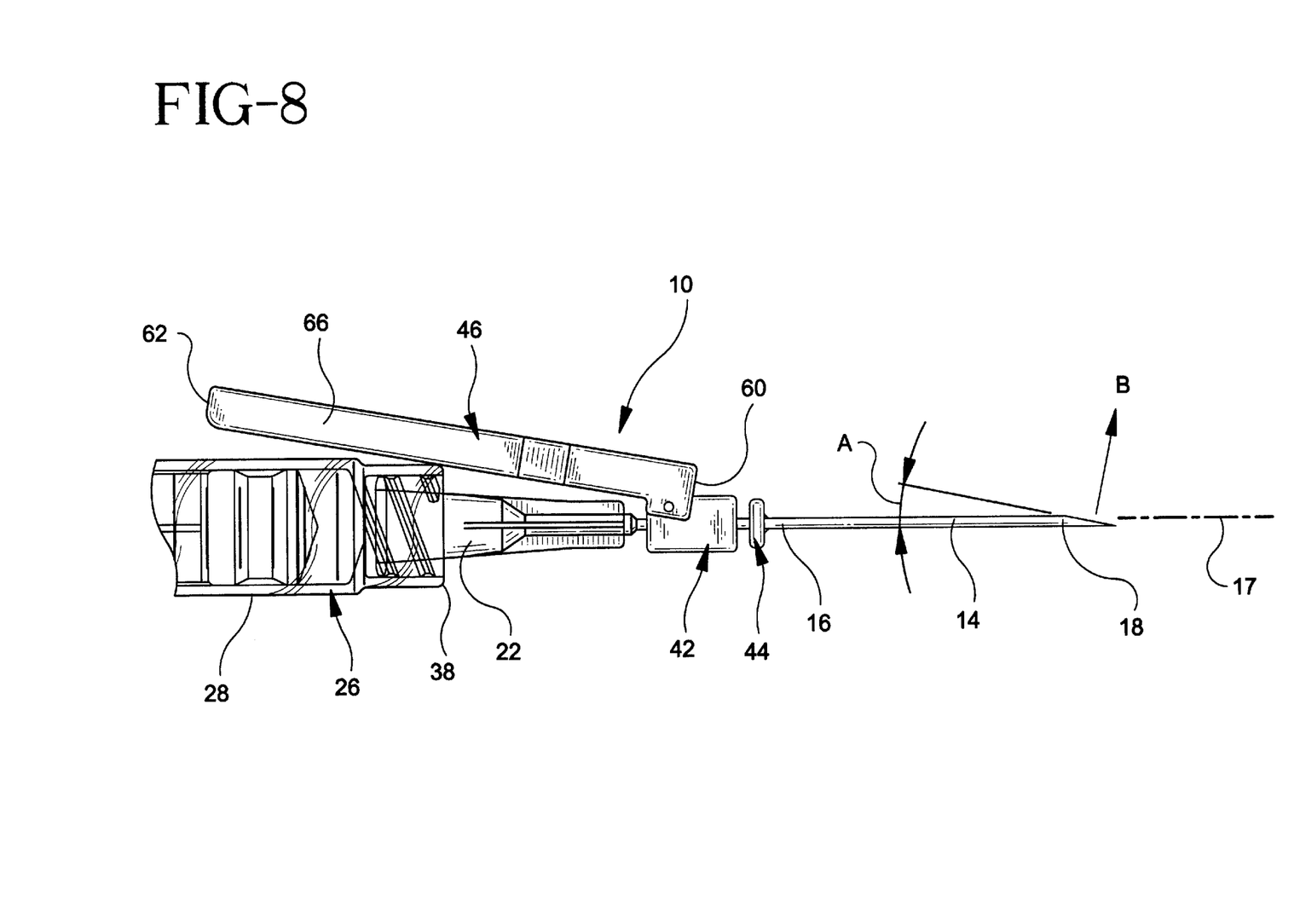
FIG. 8 is a side elevational view similar to FIG. 7, but showing the needle shield in its second position relative to the needle cannula.

Referring to FIGS. 1–8, a needle shield assembly in accordance with the subject invention is identified generally by the numeral 10. Needle shield assembly 10 is used with a needle assembly 12. The needle assembly includes a needle cannula 14 having a proximal end 16, a distal end 18 and a lumen 20 extending between the ends. Portions of needle cannula 14 at distal end 18 are beveled to define a sharp tip capable of penetrating skin tissue or piercing a stopper on a vial of medication. In particular distal end 18 of needle cannula 14 includes a sharpened tip 19 which is preferably sharpened to a bevel shape having a bevel surface 21 oriented at angle A with respect to longitudinal axis 17 of a needle cannula. Bevel surface 21 faces direction B as illustrated in FIG. 8.

Figure 1:
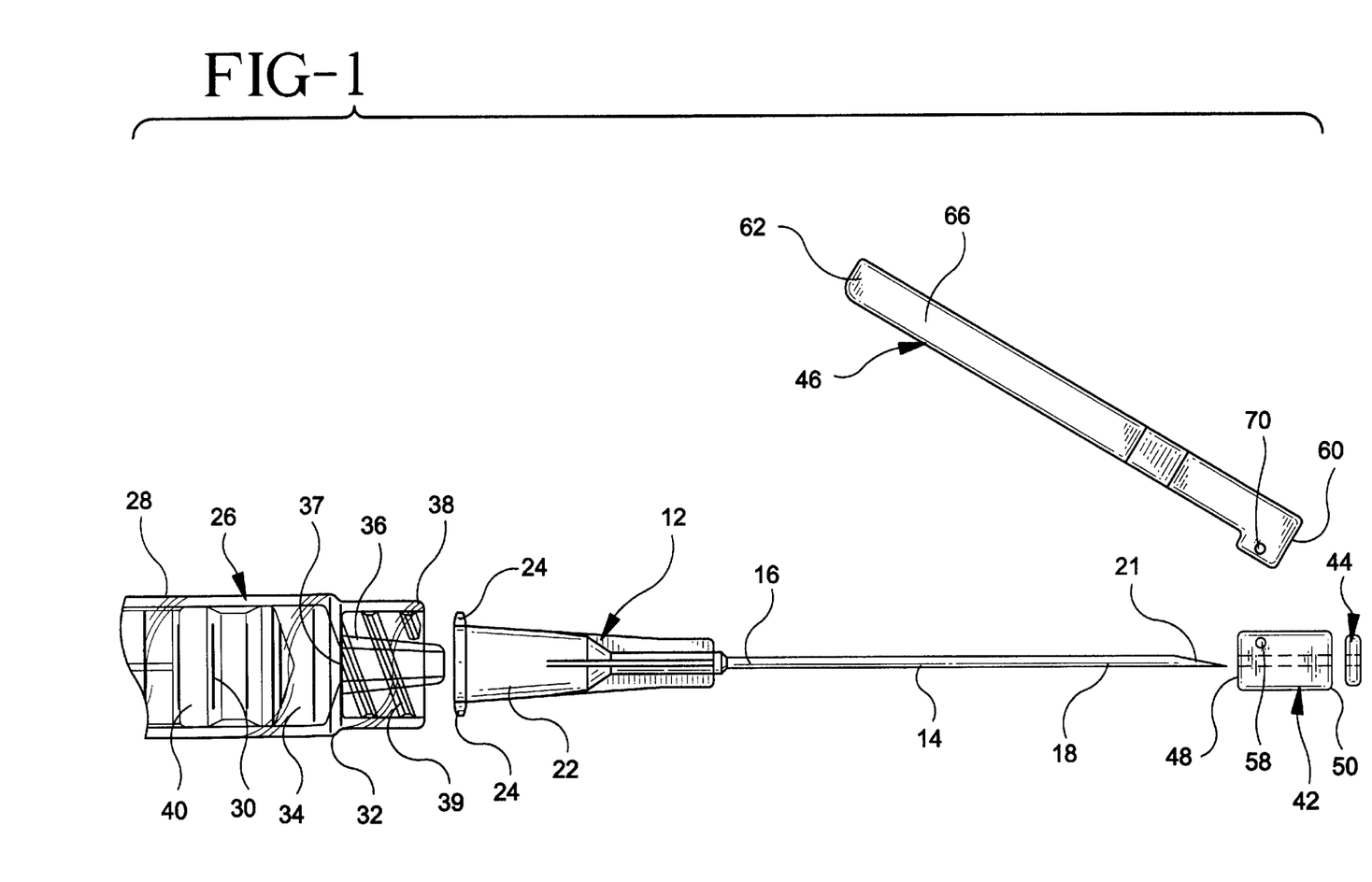
FIG. 1 is an exploded side elevational view of a shieldable needle assembly of the subject invention.

Needle assembly 12 further includes a needle hub 22 that is secured to proximal end 16 of needle cannula 14. Hub 22 includes projections 24 for threaded engagement with a luer collar on a medical implement, such as a hypodermic syringe. For example, as illustrated in FIG. 1, needle assembly 12 may be used with a hypodermic syringe 26. Syringe 26 includes a syringe barrel 28 having a proximal end (not shown), a distal end 32 and a fluid receiving chamber 34 therebetween. A tip 36 extends from distal end 32 of syringe barrel 28 and includes a fluid passageway 37 extending centrally therethrough. A collar 38 surrounds tip 36. Collar 38 includes an array of internal threads 39 for threaded engagement with projections 24 on needle hub 22.

Engagement of needle hub 22 with collar 38 places lumen 20 of needle cannula 14 into communication with fluid receiving chamber 34 of syringe barrel 28. A plunger 40 is slidably disposed in fluid receiving chamber 28. Slidable movement of plunger 40 distally in fluid receiving chamber 34 will urge fluid from chamber 34 through lumen 20 of needle cannula 14.

Figure 2:
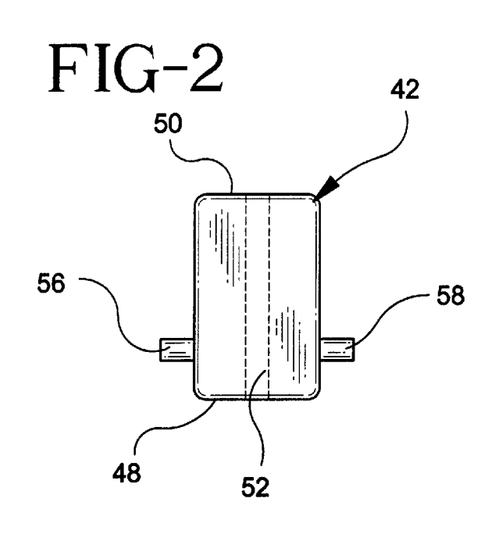
FIG. 2 is a side elevational view of the support sleeve.
Figure 3:
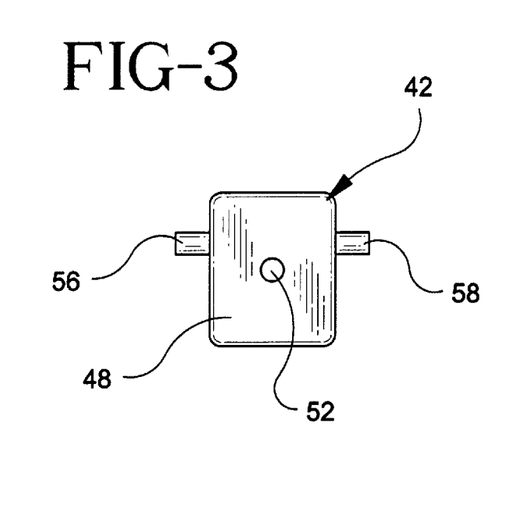
FIG. 3 is an end elevational view of the support sleeve.

Needle shield assembly 10 is effective for selectively shielding and unshielding needle cannula 14. Needle shield assembly 10 includes a rotatable support sleeve 42, a stop collar 44 and a needle shield 46. Support sleeve 42 is preferably molded from a thermoplastic material and includes a proximal end 48, a distal end 50 and a passageway 52 extending between ends 48 and 50 as shown in FIGS. 2 and 3. Passage 52 of support sleeve 42 can slidably and rotatably receive needle cannula 14. Support sleeve 42 further includes an outer surface 54 characterized by axially aligned hinge pins 56 and 58 respectively.

Stop collar 44 is an annular ring preferably having an inside diameter slightly greater than the outside diameter of needle cannula 14. Thus, stop collar 44 also can be telescoped over needle cannula 14 and, at least initially, is capable of rotation thereon. As explained further herein, stop collar 44 may initially be unitarily molded with support sleeve 42, with short thin frangible connections extending unitarily therebetween.

Figure 4:
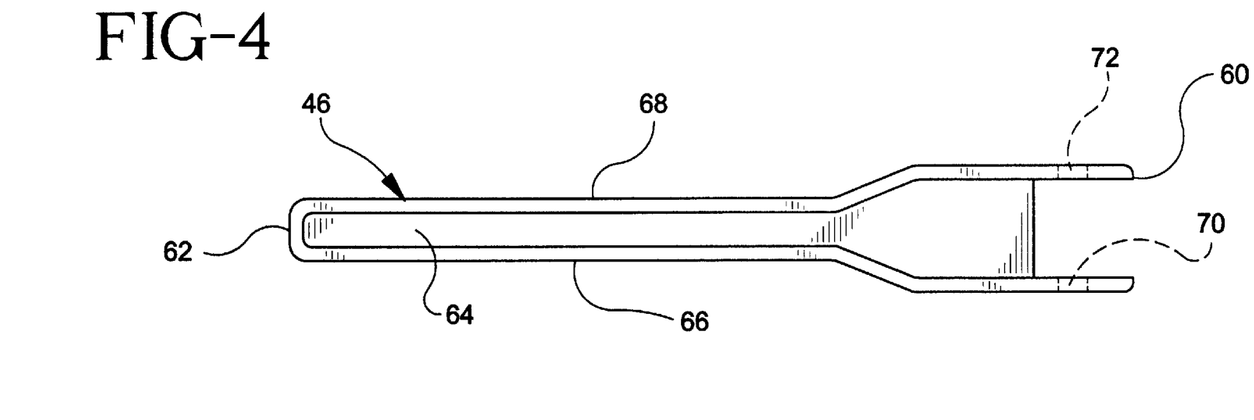
FIG. 4 is a bottom elevational view of the needle shield.

Needle shield 46 is an elongate substantially rigid structure having an open proximal end 60, and a preferably closed distal end 62 as illustrated in FIGS. 1 and 4. Portions of needle shield 46 between proximal and distal ends 60 and 62 define a substantially U-shaped structure with a base wall 64 and a pair of substantially parallel side walls 66 and 68 extending rigidly from base wall 64. Portions of side walls 66 and 68 near proximal end 60 thereof are spaced from one another by a distance preferably slightly greater than the width of support sleeve 42. Additionally, portions of side wall 66 and 68 near proximal end 60 are formed with coaxially aligned mounting apertures 70 and 72 extending therethrough. Mounting apertures 70 and 72 are dimensioned to be pivotally engaged over hinge pins 56 and 58 of support sleeve 42. Portions of side walls 66 and 68 spaced distally from mounting apertures 70 and 72 are tapered toward one another to a spacing slightly greater than the outside diameter of needle cannula 14. Side walls 66 and 68 then continue substantially parallel to one another to closed distal end 62 of needle shield 46.

Although the needle shield is rotatably connected to the support structure through a conventional hinge pins projecting outwardly from the support sleeve and engage mounting apertures in the needle shield, it is within the purview of the present invention to reverse the position of these elements so that the apertures are contained within the support sleeve and the hinge pins are part of the needle shield. It is also within the purview of the present invention to rotatably connect the needle shield and the support sleeve using a living hinge or other linkages which perform a hinge function.

Figure 5:
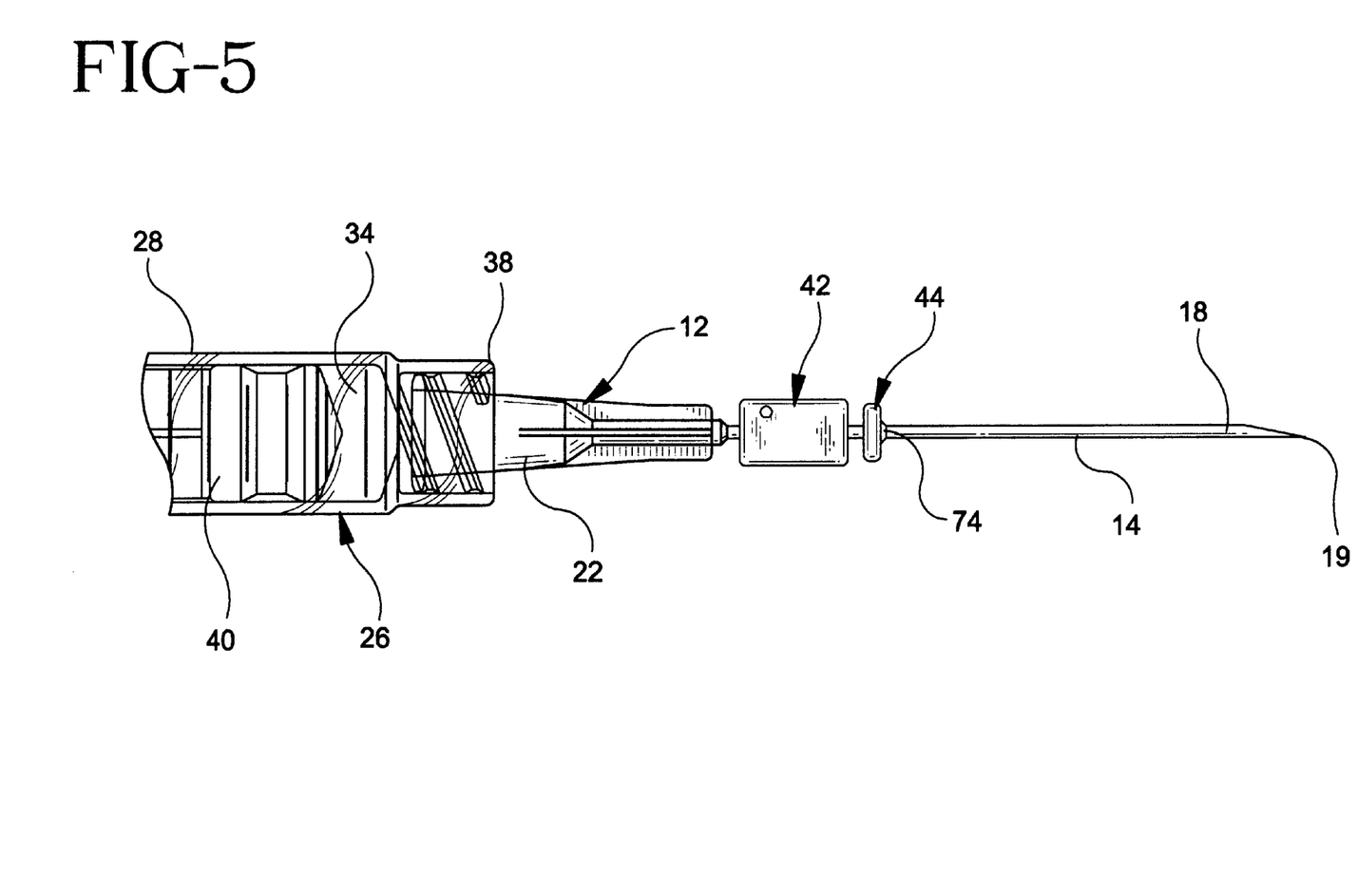
FIG. 5 is a side elevational view of the shielded needle assembly in a partly assembled condition.
Figure 6:
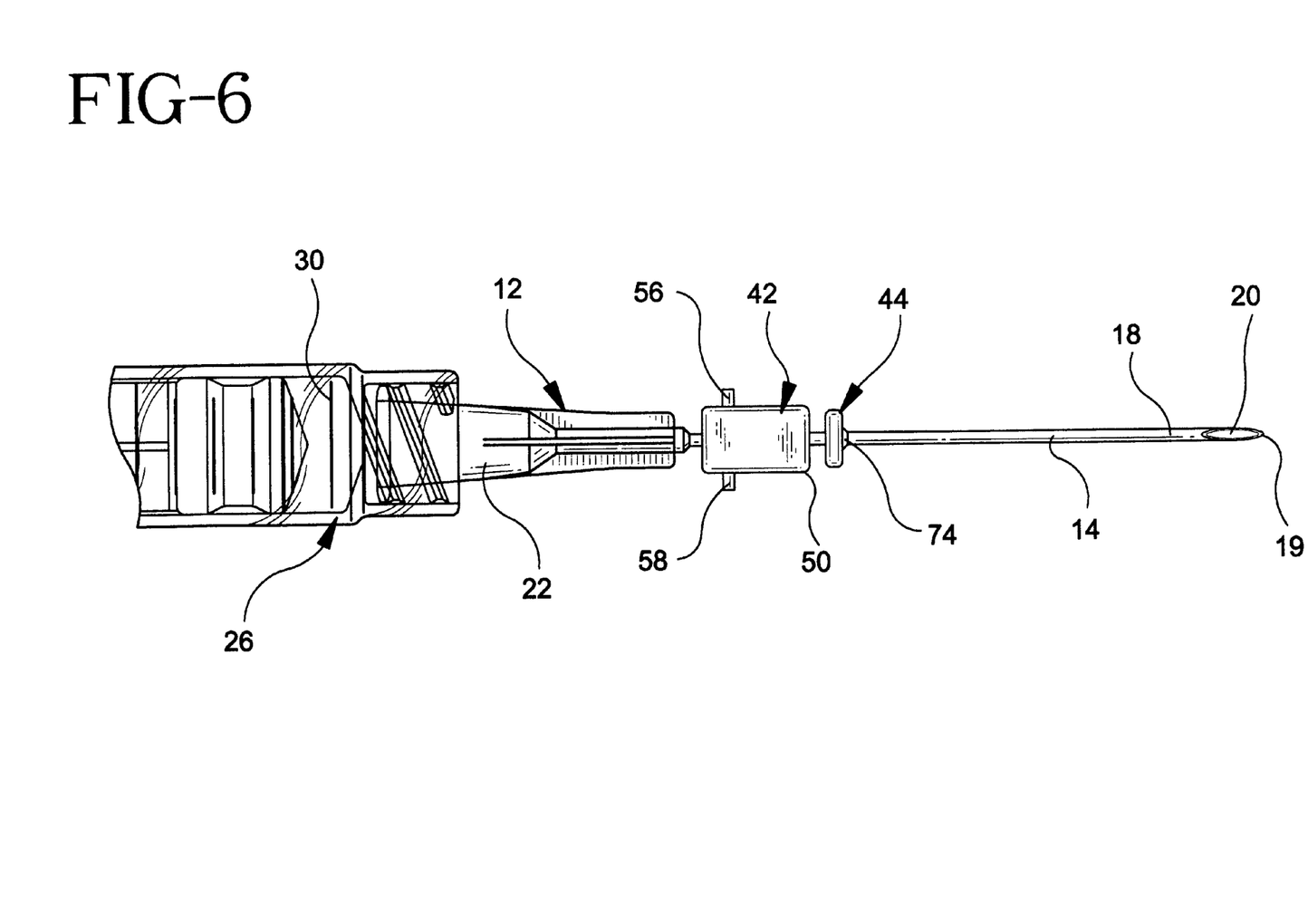
FIG. 6 is a side elevational view similar to FIG. 5, but showing the support sleeve in a different rotational orientation on the needle cannula.

Needle shield assembly 10 may be assembled by initially mounting support sleeve 42 in a distal-to-proximal direction over needle cannula 14 until proximal end 48 of support sleeve 46 is substantially adjacent needle hub 22 as illustrated in FIG. 5. As noted above, the relative dimensions of needle cannula 14 and support sleeve 42 enables support sleeve 42 to rotate relative to needle cannula 14. Assembly may continue by slidably moving stop collar 44 in a distal-to-proximal direction over needle cannula 14. The telescoping movement of stop collar 44 over needle cannula 14 is terminated when stop collar 44 is spaced slightly distally from or abutting support sleeve 42. Adhesive such as epoxy 74 may then be applied to the distal side of stop collar 44 to fixedly hold stop collar 44 in a selected position on needle cannula 14 slightly spaced from or abutting support sleeve 42. Epoxy 74 is cured in a known manner, thereby preventing further movement of stop collar 44. However, support sleeve 42 is free to rotate about needle cannula 14, and is trapped between needle hub 22 and stop collar 44. Needle shield 46 may then be mounted onto support sleeve 42 by slightly biasing side walls 66 and 68 away from one another sufficient for mounting apertures 70 and 72 respectively to snap into engagement over hinge pins 56 and 58. Thus, needle shield 46 can be hingedly rotated relative to support sleeve 42 and relative to needle cannula 14 from a first position where the needle cannula 14 is safely disposed within needle shield 46 and a second position where needle shield 46 is angularly spaced from needle cannula 14. Latch means may be incorporated into needle shield 46 and other adjacent structure, such as support sleeve 42, for releasably holding needle shield in either of its first or second rotational positions.

The rotational orientation of support sleeve 42 relative to needle cannula 14 is not significant when needle shield 46 is in its first position substantially surrounding needle cannula 14, as shown in FIG. 7. However, the rotational orientation of support sleeve 42 when needle shield 46 is rotated about hinge pins 56 and 58 and into the second position angularly spaced from needle cannula 14 as shown in FIG. 8 is an important feature of the present invention. More particularly, the rotational disposition of support sleeve 42 on needle cannula 14 enables needle shield 46 to be positioned in a location where needle shield 46 does not visually obscure the injection site and does not cause discomfort for the patient. The ability of support sleeve 42 to rotate around needle cannula 14 is an important feature of the present invention because it allows the rotation of the needle shield so that the bevel surface can be oriented with respect to the needle shield. Many practitioners prefer a bevel up orientation when injecting into a vein or subcutaneously. In this position, it is desirable to have bevel surface 21 facing the same side of the needle assembly as the needle shield when the needle shield is in its second position so that the needle shield does not interfere with positioning the syringe at a low angle close to the patient's body, for example, the patient's arm, when attempting to gain access to a vein. Also, the ability to rotate the needle shield with respect to the hub allows the needle shield to be positioned to avoid blocking the user's view of volume measuring indicia 30 on the syringe barrel. After use of needle assembly 12, needle shield assembly 10 may be employed in a substantially conventional manner by rotating needle shield 46 back toward the first position and into surrounding relationship with needle cannula 14 for preventing an accidental needle contact while needle assembly 12 is being delivered for disposal in an appropriate sharps collector receptacle.

Figure 9:
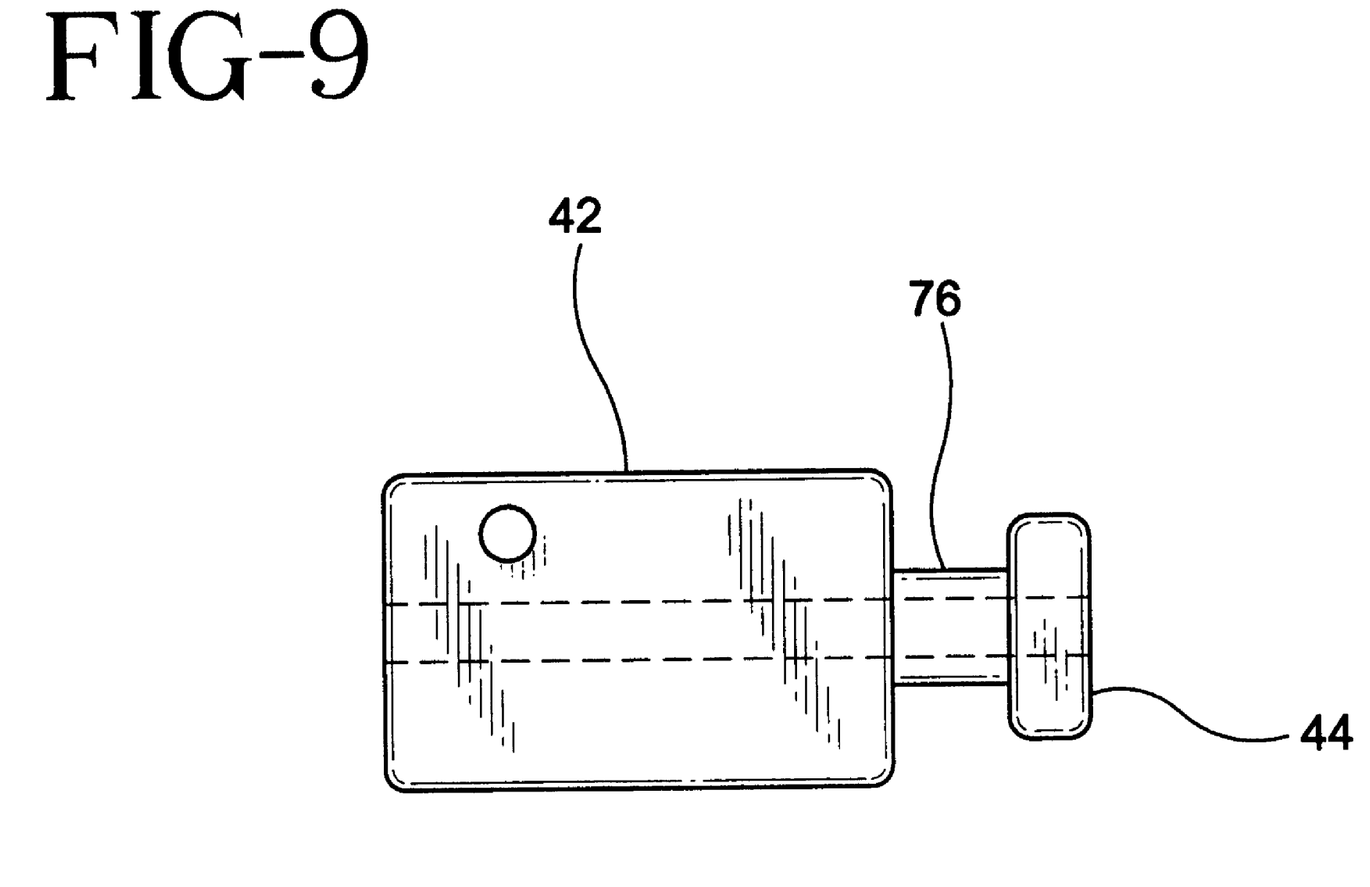
FIG. 9 is a side elevational view of a unitary support sleeve and a stop collar with a frangible connection therebetween.

As noted above, support sleeve 42 and stop collar 44 may initially be unitarily molded with one another. In this embodiment, as shown in FIG. 9, short, thin frangible connections 76 extend axially between support sleeve 42 and stop collar 44. This unitary structure of support sleeve 42 and stop collar 44 connected by frangible strip 76 is slid in a distal-to-proximal direction over needle cannula 14 until proximal end 48 of support sleeve 42 is substantially adjacent needle hub 22. Adhesive such as epoxy 74 or other means is then used to secure the distal side of stop collar 44 to needle cannula 14 as explained above. Epoxy 74 is cured in a conventional manner to securely fix both support sleeve 42 and stop collar 44 on needle cannula 14. After curing, needle shield 46 may be mounted onto support sleeve 42 by snapping mounting apertures 70 and 72 over the respective hinge pins 56 and 58. This mounting may be facilitated somewhat by the rotationally fixed disposition of support sleeve 42. Torque may then be applied to the hingedly connected support sleeve 42 and needle shield 46 to break the frangible connection strips 76 between support sleeve 42 and stop collar 44. Thus, the hingedly connected support sleeve 42 and needle shield 46 are free to rotate about needle cannula 14 as explained above.

While the invention has been described with respect to certain preferred embodiments, it is apparent that various changes can be made without departing from the scope of the invention. For example, the support sleeve and the needle shield may be unitary with one another with a thin hinge extending unitarily therebetween. The hinge may be an over center hinge that biases the needle shield into either the first position or the second position. Thus, the stop collar, the support sleeve and the needle shield conceivably all initially could be unitary with one another. The unitarily joined support sleeve and needle shield then could be separated from the stop collar by exerting rotational forces sufficient to break the frangible connections between the stop collar and the support sleeve. The assembly may vary from the assembly procedures described above. For example, the support sleeve and stop collar may be placed on the needle cannula from the proximal end of the needle cannula prior to mounting the needle hub thereto. This is a very important feature of the present invention. Placing the support sleeve directly over the needle cannula allows the assembly of the needle cannula and the support sleeve from either end of the needle cannula and before or after the attachment of the needle cannula to a hub or syringe barrel or other fluid delivery device. Assembly of the support sleeve over the proximal end of the needle cannula is desirable because it helps prevent damage to the sharpened tip of the needle cannula. Additionally, the entire needle shield assembly may be used with a hypodermic syringe or other medical implement having a needle cannula permanently and securely engaged thereon without the intermediate needle hub as described and illustrated above.

What is claimed is:

1. A needle shield assembly comprising:
    a needle cannula having a proximal end, a distal end, and a lumen therethrough;
    a support sleeve rotatably disposed around a portion of said needle cannula;
    a stop means between said support sleeve and said distal end of said needle cannula for limiting slidable distal movement of said support sleeve along said needle cannula; and
    a needle shield connected to said support sleeve for hinged rotation between a first position where said needle shield substantially encloses said needle cannula and a second position where said needle shield is spaced from said needle cannula, said needle shield and said support sleeve being rotatable about said needle cannula into a selected position for facilitating use of said needle cannula.

2. The needle shield assembly of claim 1, further including a needle hub securely mounted to said proximal end of said needle cannula for releasable connection of said needle cannula to a medical implement, said support sleeve of said needle shield assembly being disposed intermediate said stop means and said needle hub.

3. The needle shield assembly of claim 1, wherein said stop means comprises a stop collar secured to said needle cannula.

4. The needle shield assembly of claim 3, wherein the stop means further comprises adhesive for securing said stop collar to said needle cannula.

5. The needle shield assembly of claim 1, wherein said support sleeve includes a pair of diametrically opposed hinge pins extending outwardly therefrom, said needle shield including a pair of coaxially aligned mounting apertures pivotally engaged on said hinge pins of said support sleeve.

6. The needle shield assembly of claim 5, wherein said needle shield is an elongate substantially U-shaped rigid structure having a proximal end and a closed distal end, said mounting apertures of said needle shield extending through portions substantially adjacent said proximal end thereof, said needle shield being dimensioned such that said distal end of said needle shield is disposed distally of said needle cannula when said needle shield is in said first position.

7. A shielded needle assembly comprising:
- a needle assembly having an elongate needle cannula with a proximal end and a beveled distal end, a needle hub securely mounted to said proximal end of said needle cannula for removably mounting said needle cannula to a medical implement; and
- a needle shield assembly comprising a support sleeve rotatably mounted on said needle cannula at a location between said needle hub and said distal end of said needle cannula and a needle shield hingedly secured to said support sleeve, such that said needle shield is rotatable about a first axis substantially transverse to said needle cannula and about a second axis extending along said needle cannula for facilitating alignment of said needle shield relative to said needle cannula.

8. The assembly of claim 7, further comprising stop means disposed between said support sleeve and said distal end of said needle cannula for preventing removal of said support sleeve and said needle shield from said needle cannula.

9. The assembly of claim 8, wherein the stop means comprises a stop collar securely affixed to said needle cannula distally of and substantially adjacent to said support sleeve.

10. The assembly of claim 9, wherein said support sleeve includes a pair of diametrically opposed hinge pins, said needle shield being an elongate substantially U-shaped structure having a proximal end and a closed distal end, said proximal end including a pair of axially aligned mounting apertures disposed and dimensioned for pivotal mounting over said hinge pins.

11. The assembly of claim 7, further comprising frangible connections extending between said stop collar and said support sleeve, said frangible connections being breakable in response to torque applied to said support sleeve for permitting rotation of said support sleeve relative to said stop collar and relative to said needle cannula.

* * * * *